(12) United States Patent
Berger et al.

(10) Patent No.: US 7,977,284 B2
(45) Date of Patent: Jul. 12, 2011

(54) NON-ESTROGENIC ALKYLPHENOL DERIVATIVES

(75) Inventors: Paul Berger, Sugar Land, TX (US); Christie Berger, Sugar Land, TX (US)

(73) Assignee: Oil Chem Technologies, Inc, Sugar Land, TX (US)

( * ) Notice: Subject to any disclaimer, the term of this patent is extended or adjusted under 35 U.S.C. 154(b) by 0 days.

(21) Appl. No.: 12/660,991

(22) Filed: Mar. 9, 2010

(65) Prior Publication Data

US 2011/0028355 A1    Feb. 3, 2011

Related U.S. Application Data

(60) Provisional application No. 61/273,005, filed on Jul. 29, 2009.

(51) Int. Cl.
*C09K 8/584* (2006.01)
*E21B 43/00* (2006.01)

(52) U.S. Cl. ............ 507/255; 166/263; 166/270.1; 166/275; 166/305.1; 166/372; 507/203; 507/252; 507/253; 507/261; 507/262; 507/267; 568/28; 568/31; 568/35; 568/608; 568/609

(58) Field of Classification Search .......... 507/255, 507/203, 252, 253, 261, 262, 267; 166/263, 166/270.1, 275, 305.1, 372; 568/28, 31, 568/35, 608, 609

See application file for complete search history.

(56) References Cited

U.S. PATENT DOCUMENTS 6,736,211 B2 * 5/2004 Berger et al. ............ 166/270.1
7,435,709 B2 * 10/2008 Stonebraker et al.

FOREIGN PATENT DOCUMENTS

WO    WO 9706125    *    2/1997

OTHER PUBLICATIONS

Huntsman Tech Bulletin Jeffsol Alkylene Carbonates Alkoxylation of Phenols and Phenolic Resins, Copyright 2005.
White et al, "environmentally Persistent Alkylphenolic Compounds are Estrogentic", Endocrinology vol. 135 No. 1 (1994) p. 175-182.
Jobling and Sumpter—"Detergent Components in Sewage Effluent are Weakly Oestrogenic to Fish" Aquatic Toxicology—1993.
Routledge and Sumpter—"Structural Features of Alkylphenolic Chemicals Associated with Estrogenic Activity" Journ. of Biological Chemistry vol. 272, No. 6 p. 3280-3288, (1997).

* cited by examiner

*Primary Examiner* — Timothy J. Kugel

(57) ABSTRACT

A method of making phenol and alkylphenol ethoxylates non-estrogenic by inserting 1 mole of propylene oxide onto the phenolic group before proceeding with the addition of ethylene oxide or mixtures of ethylene and propylene oxide. The final phenolic products can be further reacted to form sulfates, sulfonates, phosphate esters, condensed alkylphenol alkoxylates and other derivatives of alkylphenol or phenol. Non-estrogenic phenol and alkylphenol alkoxylates and their derivatives have been found to be excellent salt tolerant, high temperature stable surfactants for oil recovery from subterranean reservoirs. These products are also useful in forming emulsions of heavy crude for transportation through pipelines.

10 Claims, 2 Drawing Sheets

NON-ESTROGENIC ALKYLPHENOL DERIVATIVES

CROSS REFERENCE TO RELATED APPLICATIONS

This application is based on provisional application Ser. No. 61/273,005, filed on Jul. 29, 2009, now expired.

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of surfactants and more specifically to a process for manufacturing non-estrogenic alkoxylated phenols and alkyl phenols and their anionic derivatives. This invention also involves the application of non-estrogenic alkoxylated phenols and alkyl phenols to various processes including but not limited to, oil recovery, heavy oil transport, de-inking, demulsification, emulsion polymerization, agricultural formulations, coatings and adhesives, mining, personal care products, laundry, and detergents products where the alkyl phenol ethoxylates and their derivatives are applied.

Alkyl phenol and phenol ethoxylates have been used extensively in the past for a wide variety of applications. These include but are not restricted to de-inking, demulsification, emulsion polymerization, agricultural formulations, oil recovery, coatings and adhesives, mining, personal care' products, laundry, and detergents products. They have been found to be among the most economical and effective surfactants. The use of phenol ethoxylates and alkylphenol ethoxylates (APEs) and their anionic derivatives has been severely restricted because they have been found to be estrogenic or their degradation products have been found to be estrogenic. A paper by White, et al in 1994 entitled "Environmentally Persistent Alkylphenolic Compounds are Estrogenic" discussed the estrogenicity of ethoxylated alkylphenols particularly octylphenol, nonylphenol (NP) and nonylphenol with one ethylene oxide (NP1EO). Jobling and Sumpter from Brunel University reported in Aquatic Toxicology1993 that Nonylphenol with one or two moles ethylene oxide (NP2EO) and Nonyl phenol with one ethylene oxide carboxylate (NP1EC) were found to be estrogen mimics. Compared to Estradiol, they found that 4-ter-butylphenol was 1,100 less estrogenic, 4-tert-octylphenol was 1,200 less estrogenic, Nonylphenol was 9,000 times less estrogenic, NP1EO 8,500 times less estrogenic, NP2EO was 9,500 less estrogenic and NP9EO was 45,500 less estrogenic. In their paper, published in the Journal of Biological Chemistry Vol. 272, No. 6 p 3280-3288 (1997), Routledge and Sumpter looked at the structural features of alkylphenolic chemicals associated with estrogenic activity. They found that altering the size and branching of the ethoxylated side chain could affect the extent of estrogenicity. They showed that addition of 2 moles of ethylene oxide to nonylphenol resulted in a 165-fold reduction in estrogenicity and addition of branched propylene oxide (PO) groups resulted in a 35,000-fold reduction in estrogenicity. Addition of two or more moles of PO resulted in complete loss of estrogenicity as also reported in WO 9706125. Addition of propylene oxide to the phenolic ring before ethoxylation results in a product that does not degrade to an estrogen precursor because the phenolic ring has been shown to degrade before the propylene oxide leaving no alkylphenol residue. WO 9706125 describes the use of propylene oxide (PO) to reduce the estrogenicity of ethoxylated phenols and alkylphenols. This patent application confirms that the addition of enough PO prior to ethoxylation will reduce or eliminate estrogenicity. The estrogenicity can be completely eliminated by adding enough PO to insure that all phenolic rings have been completely reacted with at least 1 mole of PO prior the ethoxylation. This generally will take 2 or more moles of PO for each molecule of phenolic starting material. However adding 2 or more moles PO may change the properties of the final surfactant, especially for surfactants containing low amounts of ethylene oxide. The present invention is an improvement over the existing technology by insuring that the estrogenicity of the ethoxylated phenol is completely eliminated using a minimum number of moles of PO and does not affect the final surfactant properties due to the addition of too much PO.

Recently published U.S. Pat. No. 7,435,709 discloses the use of alkylphenol in lubricating oil where the alkylphenol is made from a hydroxyaromatic such as phenol and an olefin having at least 10 carbons and greater than 80 mole % C20-C30 carbons. This product was found to be non-estrogenic however the use of such compounds in many applications is restricted because of their limited or non-water solubility. This type product would require very large amounts of ethylene oxide to render it water soluble. The present invention allows for a much lower chain length for the alkyl group attached to the alkylphenol and for the addition of much less EO to render the product water soluble.

BRIEF SUMMARY OF THE INVENTION

The primary object of the invention is to provide non-estrogenic ethoxylated phenol or ethoxylated alkyl phenol and their derivatives by adding the minimum required moles of PO using propylene carbonate without changing the final properties of the products.

Another object of the invention is to provide economical and effective non-estrogenic surfactants for a wide variety of applications.

Another object of the invention is to provide non-estrogenic surfactants for use in high temperature, high electrolyte tolerant applications.

A further object of the invention is to provide methods and compositions for emulsifying and transporting crude oil and bitumen using the non-estrogenic ethoxylated phenol or ethoxylated alkylphenol and their derivatives.

The introduction of PO using propylene carbonate to phenol and alkylphenol compounds prior to oxyalkylation with EO, as described in this invention, provides a means of reintroducing these economical and effective surfactants and overcoming objections due to their estrogenicity.

Other objects and advantages of the present invention will become apparent from the following descriptions, wherein, by way of illustration and example, an embodiment of the present invention is disclosed.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

In accordance with a preferred embodiment of the invention, there is disclosed a process for producing non-estrogenic alkoxylated phenols, alkoxylated alkylphenols and their derivatives by reacting phenol or an alkylphenol with propylene carbonate prior to ethoxylation to insure that every mole of the phenol or alkyl phenol has reacted with at least on mole of propylene oxide (PO). Full conversion can be obtained by using 1.0-1.2 moles of the propylene carbonate instead of 2-3 moles of the PO. This is described in Huntsman's Technical Bulletin entitled "Jeffsol Alkylene Carbonates Alkoxylation of Phenols and Phenolic Resins" that states that "unlike reactions in which oxiranes are employed, full reaction conversion can be obtained without employing a significant excess of alkylene carbonate. Often, conversions of aromatic hydroxyl, amine, or thiol moieties >99% can be achieved with as little as 2% excess carbonate. In contrast, a 100-300% excess of oxirane is required to insure similar conversion."

The present invention involves the addition of 1-1.2 moles of the propylene carbonate to phenols, alkyl phenol or dialkylphenols (Structure I below) to insure that all the reaction sites of the molecules of phenol, alkylphenol or dialkylphenols have been converted to at least the 1 mole PO adduct. The desired amount of the EO, PO and butylene oxide (BO) may then be added to the molecule as described below to obtain the desired performance characteristics. Structure II below summarizes the compositions of this invention:

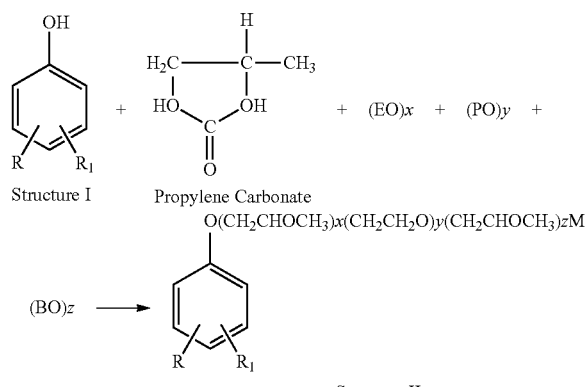

Structure I    Propylene Carbonate

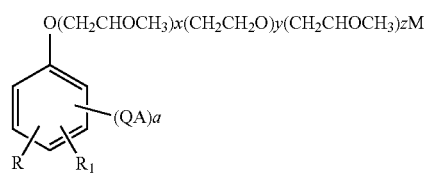

Structure II where:
R and $R_1$ are each separately and independently=H, C1-C24 linear or branched alkyl or C2-C24 linear or branched alkylene,
x=1
y=1-30
z=0-30,
M=H, $SO_3A$, $SO_4A$, COOA, $PO_4A$,
A=H, Na, K, $NH_4$, Amine, Ca, Mg,
Q=$SO_3$ or C1-C30 alkyl sulfonyl, and,
a=0-2.

Also it is within the scope of this invention to prepare non-estrogenic condensed is alkylphenol alkoxylates by reacting two or more molecules of structure II with formaldehyde to form condensed alkylphenol alkoxylates of Structure III below by methods known to those familiar with the art where n=2 or more and all the other notations are the same as above.

Structure III

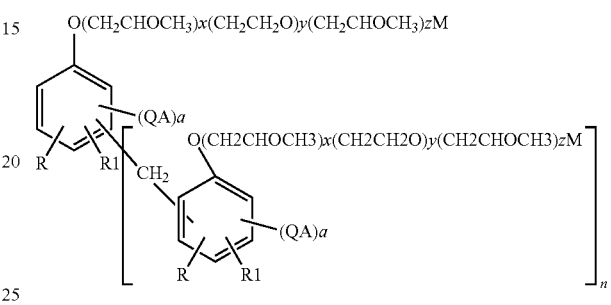

The following examples illustrate the utility of the invention as compared to the prior art.

LIST OF FIGURES

The following examples serve to illustrate that the addition of one mole of propylene oxide, using propylene carbonate to render them non-estrogenic, does not affect the performance of corresponding products compared to those where one mole of propylene oxide has not be added Example 1

Comparison of Estrogenicities for Various Alkylphenol Alkoxylates

Figure 1:
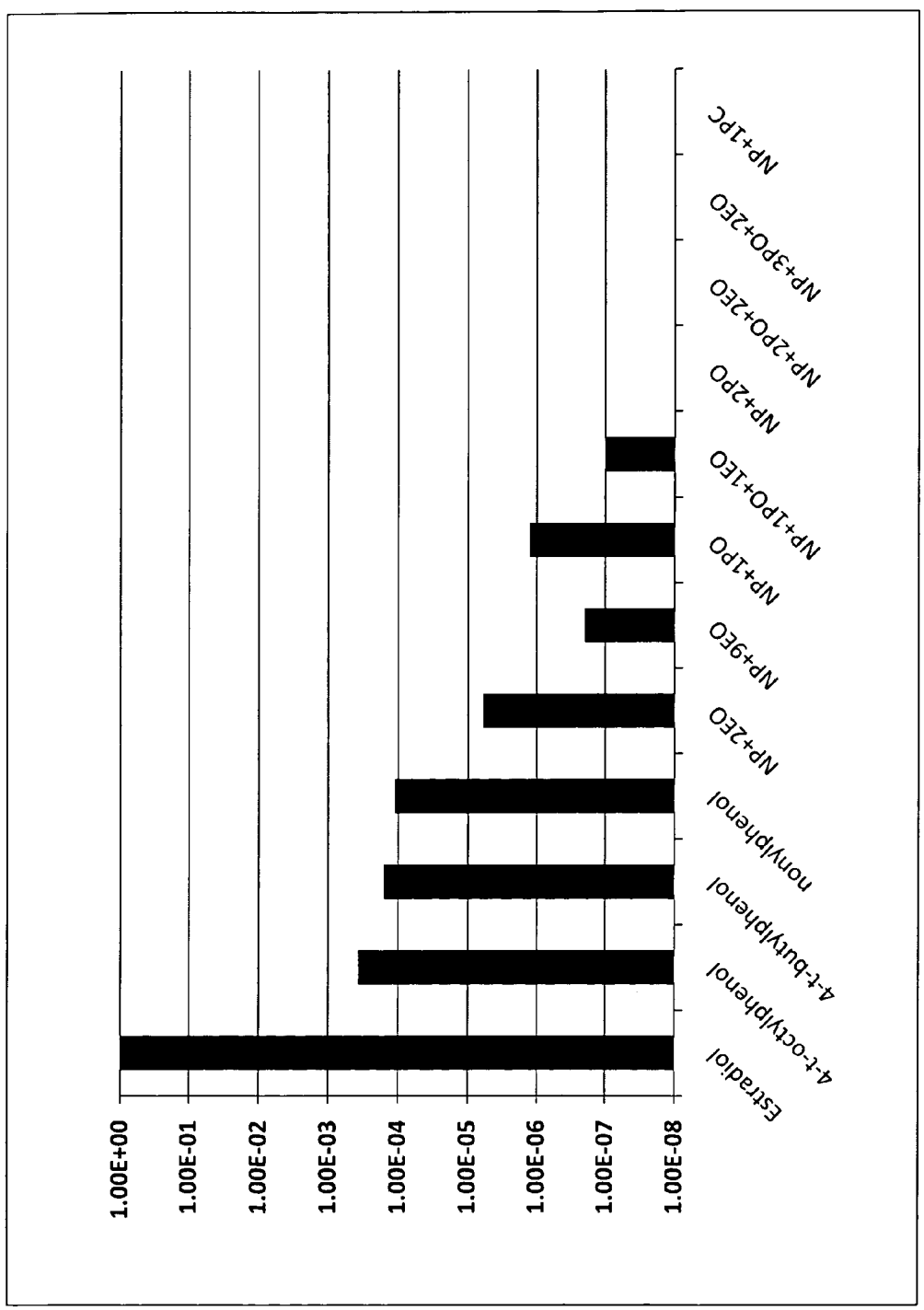
FIG. 1 shows the relative estrogenicity of various phenol derivatives compared to estradiol.
Figure 2:
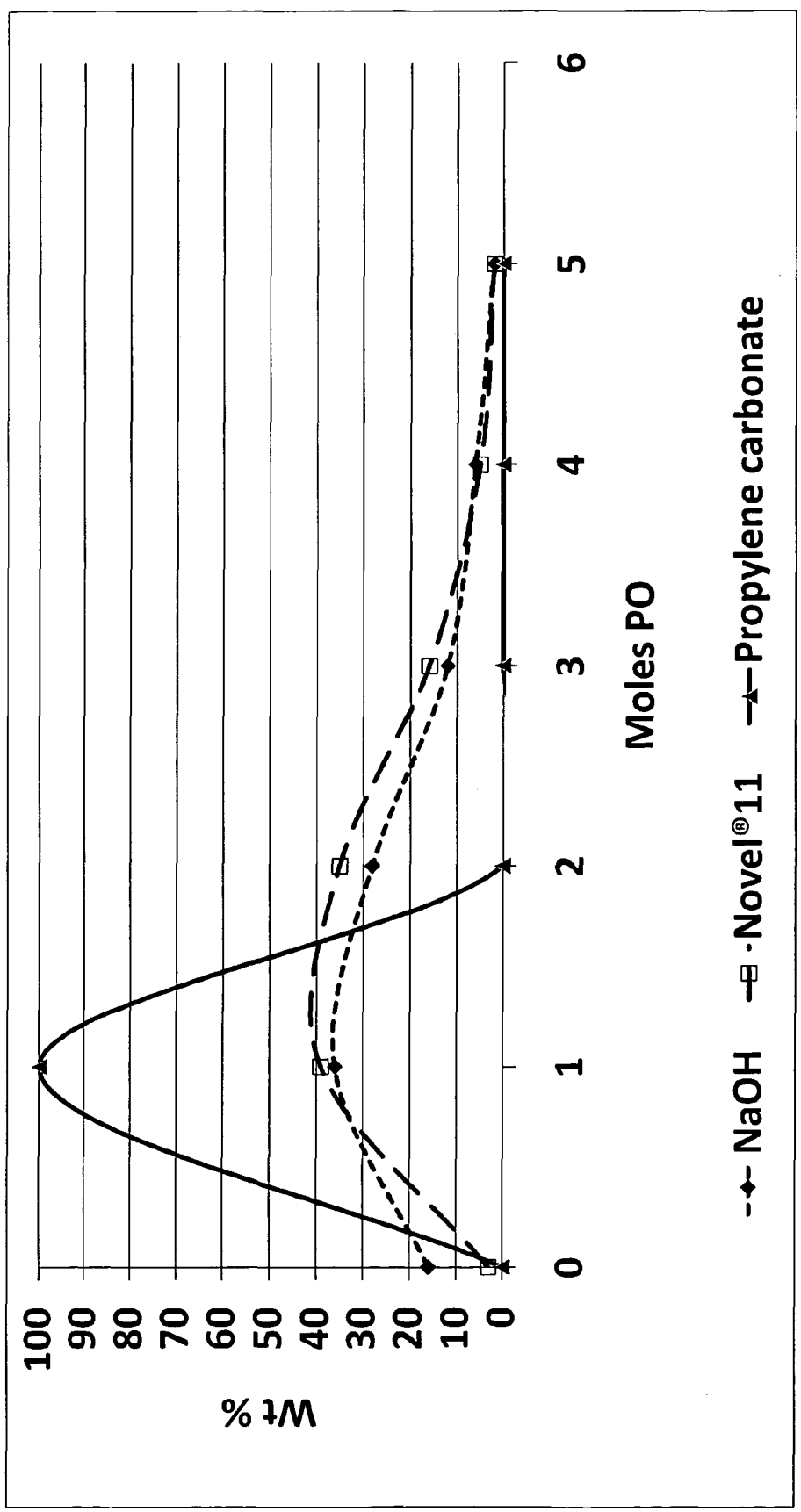
FIG. 2 shows the distribution obtained with various degrees of alkoxylation.

Table 1 and FIG. 1 show the relative estrogenicity of various alkoxylated alkylphenols compared to estradiol that is assigned an estrogenicity value of unity. From the table it can be seen that 4-t-octylphenol, 4-t-butyl phenol and nonylphenol have relatively high estrogenicity compared to the other products that are nonylphenol (NP) derivatives containing various amounts of ethylene and/or propylene oxide. Nonylphenol that has been ethoxylated, even with up to nine moles of ethylene oxide (EO) per mole of nonylphenol still shows some residual unalkoxylated nonylphenol. All products containing 2 or more moles of PO per molecule of nonylphenol do not show any detectable estrogenicity using results from a standard test procedure recognized in the field, as well as testing for stimulation of vitellogenin gene expression in trout hepatocytes (reference: Jobling et al., "Detergent Components in Sewage Effluent . . . " and White, R. et al., "Environmentally Persistent Alkylphenolic Compounds Are Estrogenic", Endocrinology, Vol. 135, No. 1, pp. 175-182). It should also be noted that the nonylphenol that has been reacted with 1 mole of propylene carbonate shows no estrogenicity and has a lower amount of free nonylphenol than the corresponding 1 mole propoxylate prepared using a standard propoxylation procedure using alkali catalyzed Propylene Oxide as is known to the art.

Table I shows that highly ethoxylated nonylphenols such as the 9 mole adduct are not estrogenic, but during sewage treatment, the alkylphenol ethoxylates are biodegraded via shortening of the ethoxylate chain to short-chain ethoxylates and carboxylic acid derivatives and finally alkylphenols, which are all estrogenic. Table I indicates that short-chain ethoxylates are less estrogenic than the unsubstituted equivalent, but substitution of the hydroxyl group with a similar-sized propylene oxide derivative results in a much greater reduction in activity. Biodegradation of the primary branched ethoxylated alkylphenols results in the production of estrogenic metabolites, but secondary hydroxyl groups cannot be oxidized to carboxylates by bacteriological activity, and therefore the biodegradation of propoxylated alkylphenols is less likely to result in the formation of estrogenic intermediates.

TABLE 1

Relative Estrogenicity

|  | Relative Estrogenicity | % free alkyl phenol |
|---|---|---|
| Estradiol | 1.000000 |  |
| 4-t-octylphenol | 0.00037 | 100 |
| 4-t-butylphenol | 0.00016 | 100 |
| nonylphenol | 0.000111 | 100 |
| NP + 2EO | 0.000006 | 0.044 |
| NP + 9EO | 0.0000002 | 0.000 |
| NP + 1PO | 0.0000013 | 1.17 |
| NP + 1PO + 1EO | 0.0000001 | 0.60 |
| NP + 2PO | 0.0000000 | 0.66 |
| NP + 2PO + 2EO | 0.0000000 | 0.00 |
| NP + 3PO + 2EO | 0.0000000 | 0.00 |
| NP + 1PC | 0.0000000 | 0.02 |

It has also been shown, via degradation studies that upon degradation propoxylated phenols or alkylphenols do not degrade into an estrogenically active material. Without being bond by any particular theory, we believe the branched propylene oxide directly attached to the phenolic ring is very slowly degraded and that the ring itself is preferentially degraded leaving no residual alkylphenol. Degradation studies have confirmed this pathway.

Example 2

Synthesize of p-nonylphenol+1PO+2EO using propylene carbonate 122.5 g of propylene carbonate (1.18M) was reacted with 234.5 g of nonylphenol using potassium carbonate catalyst. This was analyzed by NMR and Gas Chromatography (GC) and found to contain less than 0.02 wt % free nonylphenol and greater than 99.8% secondary hydroxyls indicating that essentially all the terminal hydroxyls from the nonylphenol had been reacted. This was followed by ethoxylation with 94.2 g (21.4 Moles) of ethylene oxide. This product, a nonyl phenol alkoxylate having 1 mole of PO followed by 2 moles EO, was tested for estrogenicity employing the aforementioned test procedure, and was found not to be estrogenic. It was also shown, via degradation studies that upon degradation this material did not degrade into an estrogenically active material.

Derivatives of Structure II have found application in many industrial processes including enhanced oil recovery. These products can be formulated to give surfactants that are tolerant to high concentrations of electrolyte and high temperatures. For example the surfactants of Structure II where $R_1$=$C_9$ to $C_{12}$ alkyl, $R_2$=H, $C_9$ to $C_{12}$ alkyl, x=1, y=4 to 15, z=1, M=H or $SO_3A$, A=Na, and Q=$SO_3$ have been found extremely effective as surfactants for Enhanced Oil Recovery (EOR). In particular the products where M=H have been found extremely effective in lowering Interfacial tensions (IFT) between aqueous solutions containing the surfactant and crude oil to values below $10^{-2}$ mN/m using as little as 0.05 weight percent of the surfactant. It has been found that lowering the IFT to values of below $10^{-2}$ mN/m increases the capillary number by 3 to 4 orders of magnitude and overcomes the capillary pressure in the microscope pores of the reservoir matrix allowing the injection fluid to penetrate and displace the oil. Sulfonate and sulfate derivatives containing 1 mole of PO followed by 4 or more moles of EO have been found to be extremely salt tolerant producing clear solutions in brines containing over 200,000 PPM total Dissolved Solids (TDS). The corresponding sulfonate derivatives are not only extremely brine tolerant but also can be used at temperatures exceeding 150° C.

Example 3

Table II below shows the distribution of nonylphenol homologues obtained by adding various amounts of PO as compare to adding 1 mole of the propylene carbonate to the nonylphenol. Note that the there is a wide distribution of PO homologues for all the products made using propoxylation with PO. The product made using propylene carbonate (NP+1PC) only has 0.017 wt % of un-propoxylated nonyiphenol and 99.98% of the 1 Mole of the PO adduct.

TABLE II

Homologue Distribution

| PO | NP + 1PC | NP + 1.5PO | NP + 2.5PO | NP + 3.5PO |
|---|---|---|---|---|
| 0 | 0.017% | 2% | 1% | 0.5% |
| 1 | 99.98% | 52.5% | 10.3% | 0.3% |
| 2 |  | 7.8% | 25.6% | 22.4% |
| 3 |  |  | 12.2% | 33.9% |
| 4 |  |  | 4.3% | 25.7% |
| 5 |  |  | 8.2% | 10.5% |
| 6 |  |  |  | 5.7% |

Example 4

NMR Analysis

This example shows the amount of un-ethoxylated NP+1.5PO remaining after different amounts of EO are added. Note that even after 10 moles of EO have been added there still remains 3% secondary hydroxyls indicating terminal PO groups.

TABLE III

NMR Analysis of Primary and Secondary Hydroxyls

|  | % Primary | % Secondary |
|---|---|---|
| NP + 1.5PO | <2 | >98 |
| NP + 1.5PO + 4EO | 82 | 18 |
| NP + 1.5PO + 5EO | 88 | 12 |
| NP + 1.5PO + 6EO | 91 | 9 |
| NP + 1.5PO + 10EO | 97 | 3 |

Example 5

Application to Oil Recovery

This example illustrates one of the many application to which the composition of the instant invention can be applied. One or more surfactants of structure II is dissolved in water, synthetic brine or field brine and injected into a subterranean, oil-bearing reservoir through one or more injection wells. The oil is allowed to contact the injection fluid and is recovered from one or more producing wells. The injection well may be the same as the producing well or may be a different well than the producing well.

Other ingredients may be added to the injection fluid, as is known to the art. These include viscosifiers including but not limited to polyacrylamides, xanthan gums, and viscoelastic surfactants. Solvents including but not limited to low molecular weight alcohols, glycols, and alcohol ethers. Co-surfactants such as non-ionic, anionic, amphoteric and cationic surfactants. Alkalis including but not limited to borates, silicates, carbonates, phosphates, hydroxides. Adsorption reducing agents including but not limited to polyvinylpyrrolidones, polyethylene polymers, polyglucosides, lignosulfonates, inorganic salts.

Example 6

Heavy Oil Transport

Another example of the use of the products of this invention is in the transport of heavy crude. The crude may be emulsified using products defined by structure II where the amount of ethoxylation following the addition of 1 mole of PO and the alkyl group attached to the ring are varied to give the desired emulsion stability. The emulsion of water, crude oil and surfactant can be transported through pipelines and used "as is" as a fuel source or the oil can be separated from the water and further refined.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A method for producing non-estrogenic phenol and alkylphenol compounds of the following structure

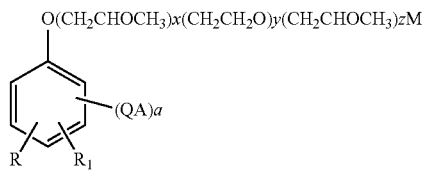

or

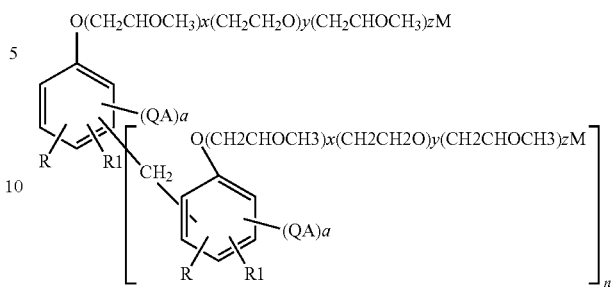

Where:
R and $R_1$ are each separately and independently=H, C1-C24 linear or branched alkyl or C2-C24 linear or branched alkylene,
x=1,
y=1-30,
z=0-30,
A=H, SO3A, SO$_4$A, COOA, PO4,
M=H, Na, K, NH4, Amine, Ca, Mg,
Q=SO$_3$ or C1-C30 alkyl sulfonyl, and,
a=0-2,
n=2 or more,
by reacting the phenol or alkylphenol precursor of the structure I where
R and $R_1$ are each separately and independently=H, C1-C24 linear or branched alkyl or C2-C24 linear or branched alkylene, Structure I

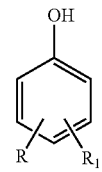

with propylene carbonate to form the one mole propoxylated adduct followed by further ethoxylation and/or propoxylation and subsequent conversion to the desired derivative.

2. The method of producing non-estrogenic phenol and alkylphenol compounds as described in claim 1 where the desired derivative is the condensation product of 2 or more moles of structure I with formaldehyde.

3. A process of recovering oil from subterranean reservoirs by injecting an oil recovery composition comprising:
   a) one or more non-estrogenic phenol or alkylphenol compounds having the following structure

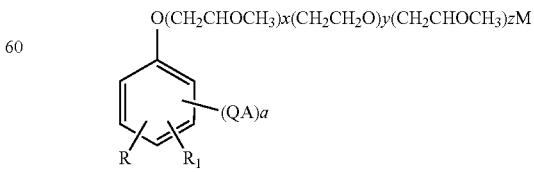

or

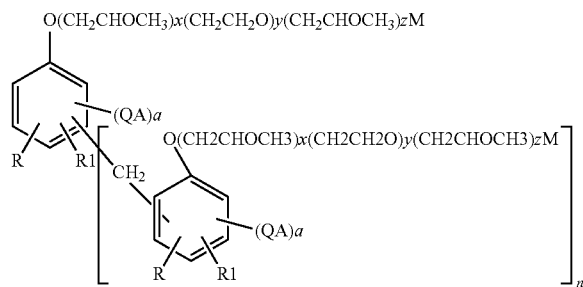

where:
R and $R_1$ are each separately and independently=H, C1-C24 linear or branched alkyl or C2-C24 linear or branched alkylene,
x=1,
y=1-30,
z=0-30,
M=H, SO3A, SO$_4$A, COOA, PO$_4$A,
A=H, Na, K, NH4, Amine, Ca, Mg,
Q=SO$_3$ or C1-C30 alkyl sulfonyl, and,
a=0-2,
n=2 or more,
b) optionally one or more co-surfactants,
c) optionally one or more co-solvents,
d) optionally one or more viscosifiers,
e) optionally one or more alkalis,
f) optionally one or more adsorption reducing agents,
g) brine,
injecting into one or more subterranean oil-containing reservoir through one or more injection wells, the solution of the oil recovery composition along with the brine allowing the oil recovery composition to contact the oil, and, recovering the oil from one or more producing wells.

4. The process of recovering oil described in claim 3 where the one or more co-surfactants are present and are chosen from the group consisting of anionic surfactants, nonionic surfactants, or amphoteric surfactants.

5. The process of recovering oil as described in claim 3 where the one or more co-solvent are present and is chosen from the group alcohol ethers, glycols, or alcohols.

6. The process of recovering oil described in claim 3 where the one or more viscosifiers are present and are chosen from the group consisting of polyacrylamides, viscoelastic surfactants, or xanthan gum.

7. The process of recovering oil described in claim 3 where the one or more alkalis are present and are chosen from the group consisting is of borates, silicates, carbonates, phosphates, or hydroxides.

8. The process of recovering oil described in claim 3 where the one or more adsorption reducing agents are present and are chosen from the group consisting of polyvinypyrrolidones, polyethylene glycols, polyalkylglucosides, lignosulfonates, or inorganic salts.

9. The process of recovering oil described in claim 3 where the brine is chosen from the group: water, synthetic brine, produced water, seawater.

10. The process of transporting heavy oil by forming an emulsion utilizing aqueous solutions of oil, water and surfactant of the structure

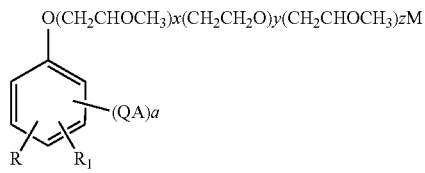

or

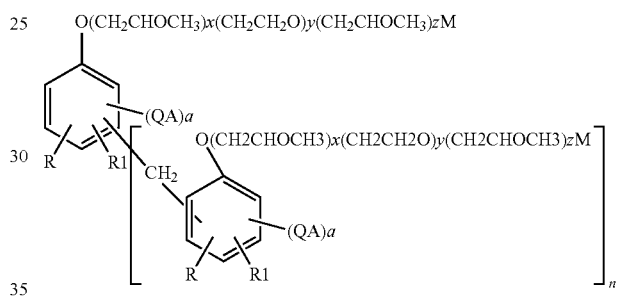

where:
R and $R_1$ are each separately and independently=H, C1-C24 linear or branched alkyl or C2-C24 linear or branched alkylene,
x=1
y=1-30,
z=0-30
M=H, SO3A, SO$_4$A, COOA, PO$_4$A
A=H, Na, K, NH4, Amine, Ca, Mg
Q=SO$_3$ or C1-C30 alkyl sulfonyl and
a=0-2,
n=2 or more.

* * * * *